United States Patent [19]

Danforth

[11] Patent Number: 5,073,168
[45] Date of Patent: Dec. 17, 1991

[54] Y-ADAPTOR AND PERCUTANEOUS SHEATH FOR INTRAVASCULAR CATHETERS

[76] Inventor: John W. Danforth, 875 25th Ave., San Francisco, Calif. 94121

[21] Appl. No.: 560,241

[22] Filed: Jul. 30, 1990

Related U.S. Application Data

[63] Continuation of Ser. No. 253,812, Oct. 5, 1988, abandoned, which is a continuation-in-part of Ser. No. 230,621, Aug. 10, 1988, abandoned.

[51] Int. Cl.⁵ .............................................. A61M 5/178
[52] U.S. Cl. ..................................... 604/167; 604/256
[58] Field of Search ............... 604/167, 169, 256, 280, 604/283, 284, 905; 137/846; 251/149

[56] References Cited

U.S. PATENT DOCUMENTS

| | | | |
|---|---|---|---|
| 2,352,642 | 7/1944 | Langdon | 137/69 |
| 3,463,159 | 8/1969 | Heimlich | 137/846 |
| 3,595,266 | 7/1971 | Brookman | 137/519 |
| 3,822,720 | 7/1974 | Souza | 137/846 |
| 3,967,645 | 7/1976 | Gregory | 137/846 |
| 4,096,860 | 6/1978 | McLaughlin | 604/167 |
| 4,106,491 | 8/1978 | Giverra | 604/167 |
| 4,211,214 | 7/1980 | Chikashige | 604/283 |
| 4,467,790 | 8/1984 | Schiff . | |
| 4,634,432 | 1/1987 | Kocak | 137/846 |
| 4,646,742 | 3/1987 | Packard et al. . | |
| 4,760,933 | 8/1988 | Christner et al. | 251/149 |
| 4,795,426 | 1/1989 | Jones | 604/256 |
| 4,822,345 | 4/1989 | Danforth . | |

FOREIGN PATENT DOCUMENTS

| | | |
|---|---|---|
| 0056103 | 7/1982 | European Pat. Off. . |
| 2645520 | 4/1977 | Fed. Rep. of Germany . |
| WO86/06285 | 11/1986 | PCT Int'l Appl. . |
| 1539253 | 1/1979 | United Kingdom . |
| 2088215 | 6/1982 | United Kingdom ............. 604/167 |

Primary Examiner—John D. Yasko
Assistant Examiner—Anthony Gutowski
Attorney, Agent, or Firm—Townsend and Townsend

[57] ABSTRACT

A Y-adapter (2) includes a check valve (22) having an entrance section (24) and a sealing section (26). The sealing section includes two or more flexible, thin, conformable sheets (48, 50) having normally abutting sealing surfaces extending axially at least twice the diameter of the therapeutic catheter (6). The sealing section collapses onto the catheter so that the patient's blood pressure seals the sheets against the catheter to prevent blood loss even during insertion and removal of the catheter. The main bore (10) is sealed adjacent the side port (20) to eliminate dead space where blood clots can form. The flexible, conformable sheets provide very little resistance to the insertion of the catheter to minimize damage to the catheter.

17 Claims, 4 Drawing Sheets

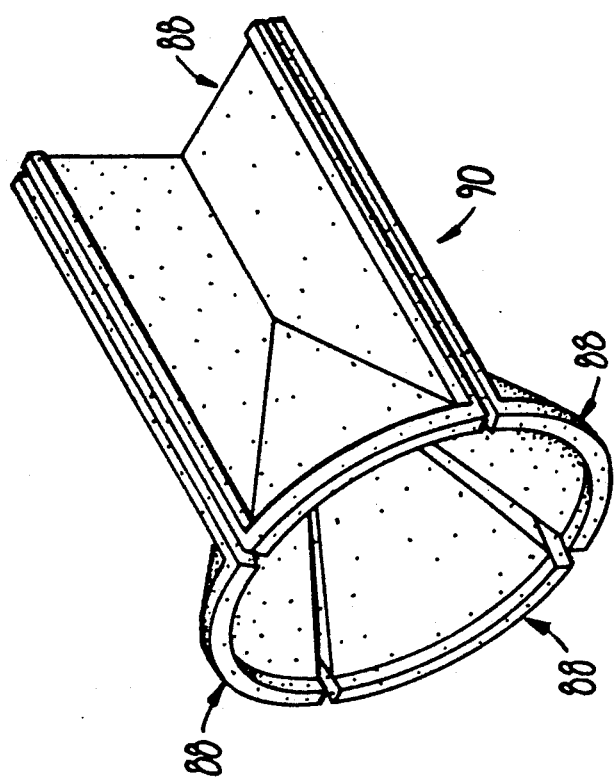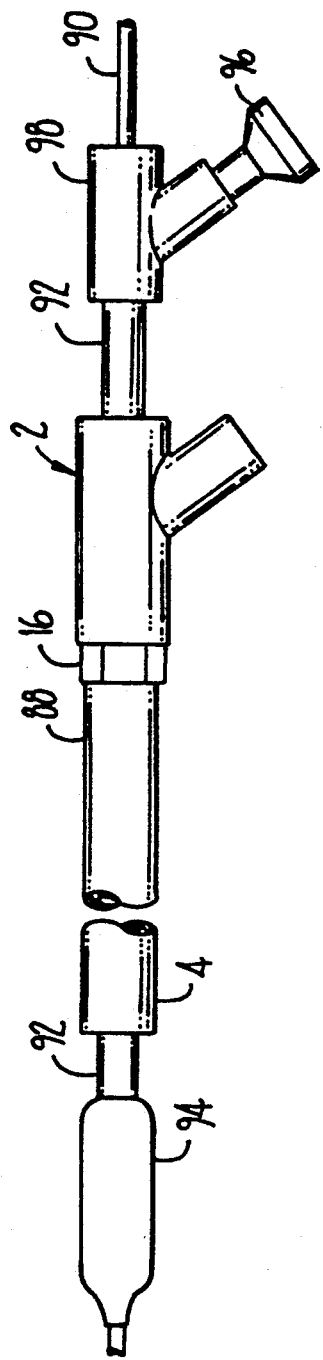

Y-ADAPTOR AND PERCUTANEOUS SHEATH FOR INTRAVASCULAR CATHETERS

This is a continuation of Ser. No. 07/253,812 filed Oct. 5, 1988, now abandoned, which is a continuation-in-part of Ser. No. 07/230,621 filed Aug. 10, 1988, now abandoned.

FIELD OF THE INVENTION

The following invention refers to a Y-adapter to be used during the course of an angioplasty, or similar procedure, wherein a therapeutic catheter must be inserted into, and removed from, a closed catheter system (e.g., a guiding catheter system) that previously has been installed within a region of the body containing liquids under pressure (e.g., the vascular system). In this circumstance the Y-adapter functions to: (1) provide a port of entry for the therapeutic catheter within the otherwise closed/pressurized catheter system and (2) provide a seal between the therapeutic catheter and the aforementioned catheter system. This seal functions to limit the loss of systemic pressure and fluid (e.g., blood) sustained during the process of introducing and removing the therapeutic catheter.

This invention can be modified into the configuration of a vascular sheath that can be used to expedite the percutaneous intravascular introduction and removal of a variety of both diagnostic and therapeutic catheters with minimal systemic fluid (e.g.. blood) and/or pressure loss. Unless otherwise specified, however, the following text will refer to the Y-adapter application of this invention.

BACKGROUND OF THE INVENTION

Therapeutic catheters are frequently introduced into the body by means of guiding catheters. In the case of intravascular procedures, the system containing the guiding catheter must be closed and pressurized to prevent the development of blood loss and hemodynamic compromise during the performance of the therapeutic procedure. To permit the introduction and exchange of therapeutic catheters within this relatively closed system, several adapters have been created that: (1) provide a port of entry for the therapeutic catheter and (2) provide a seal between the therapeutic catheter and the aforementioned system. The seal functions to limit the amount of systemic pressure and/or blood loss that transpires during the course of introducing or exchanging a therapeutic catheter within the guiding catheter system. These adapters all contain a side port that can be used for various purposes, such as monitoring intravascular pressures, flushing the guiding catheter system, evacuating blood clots from the system, and the like. Because of their configuration, these adapters are called Y-adapters. Although similar in many respects, these devices differ with respect to the design of the sealing element or check valve.

One type of sealing element consists of a membrane, disposed perpendicular to the axis of the Y-adapter, containing a central perforation, that accommodates the therapeutic catheter. Initial insertion of the therapeutic catheter through the perforation stretches the membrane slightly to create an effective seal. An example of this type of Y-adapter is the model 006057 introduced by USCI Bard Catheter Systems of Billerica, MA.

There exist several functional limitations intrinsic to this type of sealing design among them the following: (1) the seal cannot be adjusted to accommodate to the various configurations and dimensions of current generation catheters, (2) the seal cannot function properly following removal of the therapeutic catheter contained therein (a circumstance that invariably transpires during the process of exchanging therapeutic catheters, a common occurrence during the course of an angioplasty) and (3) the seal tends to deteriorate following the repeated introduction of catheters through the membrane. In addition, the use of Y-adapters containing membrane sealing devices frequently exposes the therapeutic catheter to considerable trauma during the process of introducing and removing the catheter across the membrane.

Because of these limitations, among others the use of Y-adapters containing membrane sealing devices has been largely replaced by the use of adapters containing adjustable O-ring sealing devices. There currently exist two such devices, model 23242 manufactured by Advanced Cardiovascular Systems (ACS) of Mountain View. California and the dual valve rotating Y-adapter, catalogue number Y-7200 manufactured by American Edwards of Irvine California. In the case of these devices, the deformable O-ring is mounted coaxial with the main bore of the adapter, within a threaded element Rotation of the threaded element, relative to the adapter compresses the deformable O-ring resulting in a progressive reduction in the luminal dimensions of the O-ring. A seal is created when the luminal dimensions of the O-ring approximate the corresponding outer dimensions of the therapeutic catheter installed therein. This O-ring design offers several advantages relative to the aforementioned membrane design because it can be adjusted to maintain an effective seal regardless of the presence, absence, or dimensions of the catheter installed therein.

Despite these advantages, the seal created by the O-ring does not function automatically. As a result the use of adapters containing this type of sealing device requires continuous attention during the process of therapeutic catheter introduction, manipulation and withdrawal, a circumstance that is both distracting to the operator and counterproductive to the performance of an angioplasty, a complex and mentally demanding procedure. In addition, the O-ring design does not permit the maintenance of a satisfactory seal throughout the process of introducing or removing the therapeutic catheter, regardless of the attentiveness of the operator. For example, the insertion of a therapeutic catheter within a Y-adapter containing an O-ring sealing device requires the operator to adjust the luminal dimensions of the O-ring to accommodate the therapeutic catheter dimensions before introducing the catheter a circumstance that invariably compromises the sealing capacity of the device and permits considerable fluid loss (e.g.. blood loss) from the pressurized system. A similar circumstance transpires during the course of removing a therapeutic catheter from the Y-adapter. Thus, blood loss inevitably occurs during the process of both introducing and removing therapeutic catheters from pressurized guiding catheter systems containing O-ring sealing devices. Although it is tempting to speculate that the dimensions of the O-ring could be adjusted to permit the gradual introduction of the therapeutic catheter with minimal interruption of the seal, it must be recognized that this circumstance exposes the relatively delicate and expensive therapeutic catheter to considerable potential trauma — an unacceptable circumstance.

In short, the use of all currently available Y-adapters, during the performance of an angioplasty, or similar therapeutic procedure, wherein a therapeutic catheter must be installed within a relatively closed and pressurized guiding catheter system, invariably results in blood loss from the system, during the process of catheter introduction, manipulation, exchange and withdrawal. Although blood loss per se constitutes an adverse potential of these devices for the patient, it must be recognized that this circumstances also directly exposes the operator to potential contaminants within the patient's blood stream. The accumulation of blood within the guiding catheter system, an inevitable consequence of backbleeding through the Y-adapter check valve, also permits the formation of blood clots within the guiding catheter system, that could precipitate a stroke or heart attack, if inadvertently dislodged and introduced into the patient's circulation (which is in direct communication with the guiding catheter system). The presence of blood within the translucent Y-adapter also obscures the lumen within the adapter, further complicating the process of introducing the often small and delicate therapeutic catheters within the confines of the device.

To limit the extent of back-bleeding sustained during the process of introducing and removing the therapeutic catheter through the O-ring sealing device, a relatively stiff conical valve has been installed within the main bore of the American Edwards device, coaxial with, and proximal to, the O-ring check valve. Although this arrangement is partially effective this combination of valves: (1) does not function automatically, (2) does not provide an adequate seal throughout the process of introducing and removing a therapeutic catheter and (3) it exposes the therapeutic catheter to an increased risk for potential trauma during the process of manipulating the catheter across both valves in either direction. This latter circumstance derives from the fact that the presence of the in-line conical valve substantially contributes to the intrinsic resistance of the device to the passage of a therapeutic catheter. As a result substantially increased force must be applied to manipulate therapeutic catheter through this device relative to the ACS adapter.

Because the Y-adapter is interposed between the patient and the transducers used to monitor the patient's hemodynamic status, within the guiding catheter system, disruption of the Y-adapter seal profoundly compromises the operators ability to monitor the hemodynamic status of the patient. Because the seal must be compromised during virtually every aspect of the angioplasty procedure (e.g., therapeutic catheter introduction, withdrawal and exchange) to permit manipulation of the therapeutic catheter relative to the Y-adapter, and because this circumstance substantially impairs the operator s ability to assess the status of the patient during the procedure, most operators have become accustomed to intermittently interrupting the angioplasty procedure in order to close the seal temporarily and thus reassess the patient's hemodynamic status, an approach that contributes to the duration, complexity and potential risk of the angioplasty procedure.

In addition to the aforementioned functional limitations of conventional Y-adapters, it must be recognized that these devices frequently bind onto the therapeutic catheters installed therein (thus compromising the operator s ability to determine the amount of resistance incurred by the distal aspect of the catheter during introduction of the catheter across a stenotic lesion).

Furthermore, all currently available Y-adapters: (1) contain considerable dead space that permits the accumulation of blood clots. (2) provide inadequate seals when used in conjunction with asymmetric systems (e.g., monorail systems) and (3) frequently permit the inspissation of air bubbles within the guiding catheter system.

In summary, there currently exists no Y-adapter that contains a sealing element that: (1) functions automatically, (2) functions satisfactorily throughout all phases of catheter introduction and withdrawal and that (3) generates minimal resistance to catheter introduction.

Although the primary application of the device described herein is directed to a Y-adapter that meets these criteria, it must be recognized that this invention can be modified into the configuration of an intravascular sheath (such as one made by Cordis Corporation of Miami, Florida as Catheter Sheath Introducer System) that can be used to expedite the percutaneous introduction of a variety of both therapeutic and diagnostic catheters within the vascular system with minimal resistance, blood and/or pressure loss. Although considerably different in appearance the components of a sheath and a Y-adapter are substantially similar. In the case of sheaths, the sealing element consists of an elastomeric gasket that circumferentially contains the catheter installed therein. Although the seal created by the gasket is generally effective, the resistance generated by this sealing element to the passage of a catheter is generally considerable. In fact, this type of sealing element occasionally binds to the catheter contained therein, thus substantially compromising the operator's ability to complete the intended procedure. In addition the gasket check valve tends to leak when crossed with simply a guide wire or small caliber catheter. This latter circumstance derives from the fact that the leaflets of the gasket check valve are designed to conform to the outer surface of a catheter of conventional dimensions. The insertion of a guide wire or small catheter across the check valve of a conventional sheath results in incomplete coaptation of the leaflets and hence incompetence of the valve.

SUMMARY OF THE INVENTION

The present invention is directed to an adapter for introducing a therapeutic catheter, guide wire or like device into a guiding catheter system during medical procedures. For purposes of simplicity the various devices which may be inserted through the adapter will usually be referred to collectively as therapeutic catheter or just catheter. The guiding catheter has its outer end secured to a first end of a main bore in the adapter. The adapter includes a check valve positioned within the main bore of the body of the adapter which prevents fluid flow in a reverse direction from the first end, that is the end connected to the guiding catheter, towards the second end before and after a therapeutic catheter has been inserted through the check valve in a forward direction from the second end of the main bore towards the first end of the main bore.

The check valve includes an entrance section, towards the second end of the main bore, and a sealing section, toward the first end of the main bore. The sealing section includes flexible, conformable sheets having normally abutting sealing surfaces between which the therapeutic catheter passes. The highly conformable nature of the material, from which the conformable sheets are made, provides an effective seal between the therapeutic catheter and the check valve by virtue of the fluid (e.g., blood) pressure compressing the sheets against one another and/or the outer surface of the therapeutic catheter contained therein. The axial length of the sheets must be about at least twice the transverse dimension of the therapeutic catheter to permit proper functioning of the sealing device.

The sheets preferably have an inner surface which provides very little resistance to the insertion and removal of the therapeutic catheter. This is important because therapeutic catheters are often thin, fragile and easily damaged. The low resistance could be provided by the nature of the sheets or by a lubricant compatible with the appropriate body fluid of the patient. An example of a material which is expected to be suitable is that made by Baxter-Edwards Laboratories of California as Hydrocross.

Since the sealing surfaces are preferably made of relatively flimsy, flexible, conformable sheets of material, they may have a tendency to prolapse when first subjected to fluid pressures with no therapeutic catheter in place or to accordion back during the process of catheter removal and thus lose proper sealing effectiveness. To circumvent these problems, appropriate structure is preferably used to maintain the sheets in a desired, typically extended, at-rest shape.

The check valve preferably seals the interior of the main bore at a first position along the main bore so that fluid entering into the main bore through the first end can move only to the first position. This typically is achieved by securing the circumference of the check valve against the wall of the main bore at the first position. Passage in the reverse direction through the check valve itself is prevented by the configuration of the check valve.

The main bore of the Y-adapter contains a side opening preferably located between the first end of the bore and the first position at which the check valve sealingly engages the main bore adjacent to the first position. This configuration helps to eliminate any dead space in the main bore between the supplemental opening and the check valve. The substantial elimination of the dead space helps to diminish the potential for this device to accumulate blood clots within the main bore.

The sealing of the check valve against the main bore at the first position is preferably at an angle extending from the supplemental opening in a radial or transverse direction away from the supplemental opening and in the forward direction towards first end of the main bore. This orientation of the check valve further reduces the thrombotic potential of the device because it functions to both limit the amount of dead space contained within the main bore of the Y-adapter and limit the amount of turbulence that develops within the device during the process of flushing the adapter with fluid entering the main bore from the side port and exiting the device from the first end. Intermittent flushing is required to evacuate blood clots that accumulate within the main bore of the adapter. The development of turbulence can be counterproductive in this regard.

During use the check valve creates an effective seal that prevents blood loss through the check valve before insertion, during insertion, during manipulation and during removal of the catheter. That is, when the therapeutic catheter begins to enter the sealing section of the check valve, the proximal aspect of the therapeutic catheter begins to deflect apart the conformable sheets. The pressure within the main bore (a function of the patient's systemic blood pressure) forces the sheets to conform to the outer surface of the catheter installed therein, thus forming a seal between the adapter and the catheter. Because of the length of the sheets this seal develops before the tip of the catheter exits from the sealing device and enters the main bore of the adapter. Once the valve exit has been opened, there already exists an effective, relatively long sealing area of the sheets against the therapeutic catheter. The axial sealing distance is sufficiently long to prevent the migration of the fluid (typically blood) between the therapeutic catheter and the conformable sheets so to maintain the seal.

Hence, the use of this device will permit the maintenance of an adequate seal, for the preferably closed/pressurized guiding catheter system, throughout all phases of introducing, manipulating and removing the therapeutic catheter. As a result, the use of this device will substantially curtail the development of back-bleeding and its consequences (e.g., patient blood loss, blood and thrombus accumulation within the guiding catheter system, thromboembolic complications sustained as a result of the inadvertent dislodgement of the aforementioned blood clots into the systemic circulation of the patient, operator exposure to potential contaminants within the patient's blood stream, etc.). The automatic nature of the sealing device will eliminate the need for continual readjustment and permit the operator to focus his/her attention on the procedure at hand. In this regard, the use of this device will permit the operator to continuously monitor the patient's hemodynamic status without interrupting the procedure for this purpose.

The sealing device will effectively accept a variety of catheter configurations and it will permit the introduction of therapeutic catheters with minimal resistance relative to conventional sealing devices. This latter feature will enable the operator to better appreciate the resistance incurred by the proximal aspect of the therapeutic catheter when introduced across a vascular obstruction/stenosis relative to conventional sealing devices. Because the propensity for the sealing device to traumatize the therapeutic catheter is directly related to the force required to advance the catheter across the sealing device, a function of the intrinsic resistance of the device, it is likely that this sealing device will confer minimal catheter trauma relative to conventional sealing devices, because of this low-resistance feature. Because the inspissation of air bubbles (that have embolic potential when introduced into the systemic circulation) tends to occur consequent with the introduction of a therapeutic catheter across a high resistance sealing device, it is entirely conceivable that the use of this device should result in a reduction in the incidence with which air bubbles become entrained within the guiding catheter system and systemic circulation, during the performance of an angioplasty or similar intravascular therapeutic procedure. In short, the use of this device will enhance the safety, efficacy and efficiency of an angioplasty or similar procedure wherein a therapeutic catheter must be installed into, manipulated within, and subsequently removed from, a preferably closed and pressurized guiding catheter system.

Other features and advantages of the invention will appear from the following description in which the preferred embodiments have been set forth in detail in conjunction with the accompanying drawings.

BRIEF DESCRIPTION OF THE DRAWINGS

FIG. 6 illustrates an alternative embodiment of the check valve of FIG. 5 showing use of four sheets.

FIG. 7 is an overall side view showing the Y-adapter of FIG. 1 in use during angioplasty.

DETAILED DESCRIPTION OF THE PREFERRED EMBODIMENTS

Figure 1:
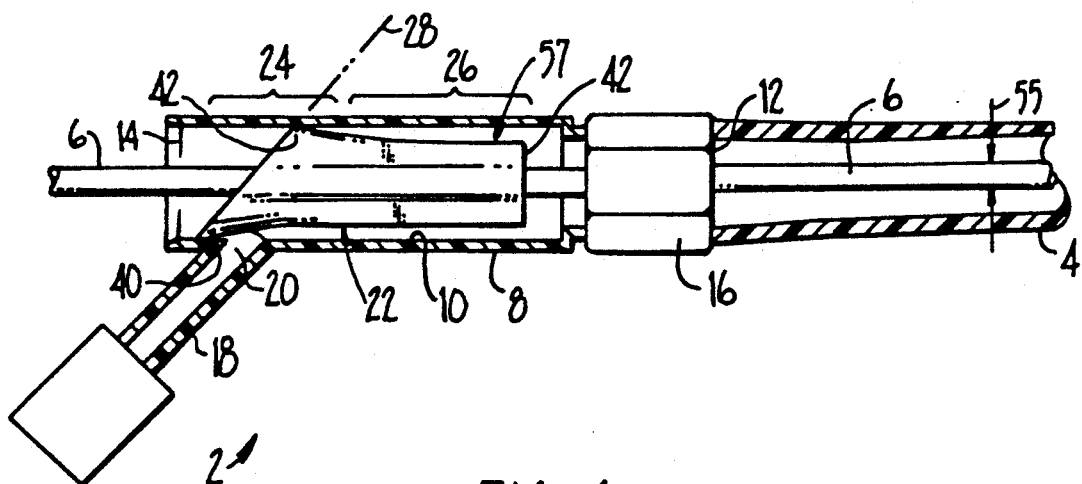
FIG. 1 is a side cross-sectional view of a Y-adapter embodiment of the invention with a simplified check valve and a therapeutic catheter in place.

Referring now to FIG. 1, a Y-adapter 2 is shown in conjunction with a guiding catheter 4 and a therapeutic catheter 6. The therapeutic catheter 6 may be of various types including an angioplasty dilation balloon catheter, a fiberoptic laser catheter, an atherectomy catheter, and so forth. The preferred embodiment will be described as used with guiding catheter 4 inserted into the vascular system of a patient. However, the invention is not limited to such use.

Adapter 2 includes a body 8 having a main bore 10 extending between a first end 12 and a second end 14. Guiding catheter 4 is secured to first end 12 by connector 16. Body 8 includes a side branch 18 having a side port or supplemental opening 20 fluidly coupled to the interior of main bore 10 between first and second ends 12, 14. Side port 18 is used for conventional therapeutic purposes, such as flushing and monitoring of the patient's systemic pressure.

Figure 2:
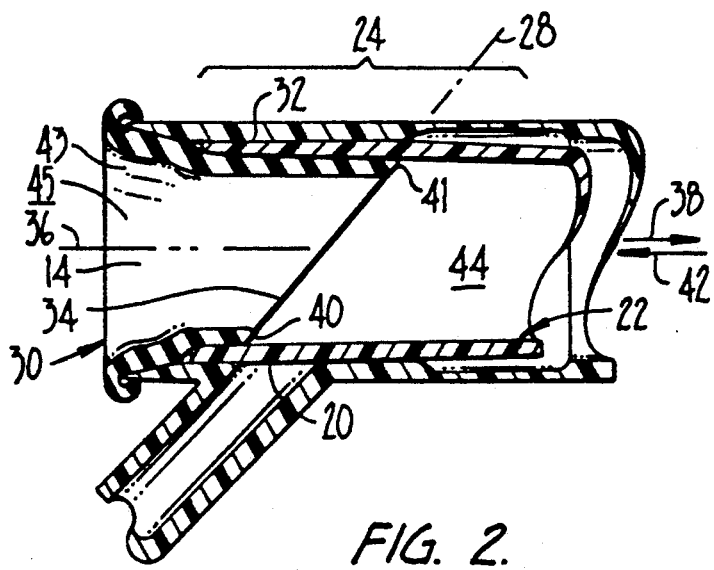
FIG. 2 is an enlarged cross-sectional view of a portion of the adapter of FIG. 1 without the therapeutic catheter in place.
Figure 3A:
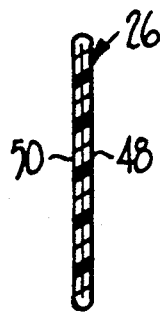
FIGS. 3A and 3B are cross-sectional views taken along line 3A—3A in FIG. 3 without and with the therapeutic catheter of FIG. 1 in place.
Figure 3B:
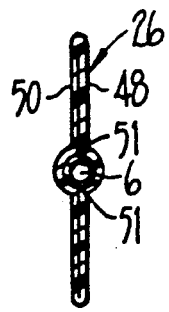
Figure 3:
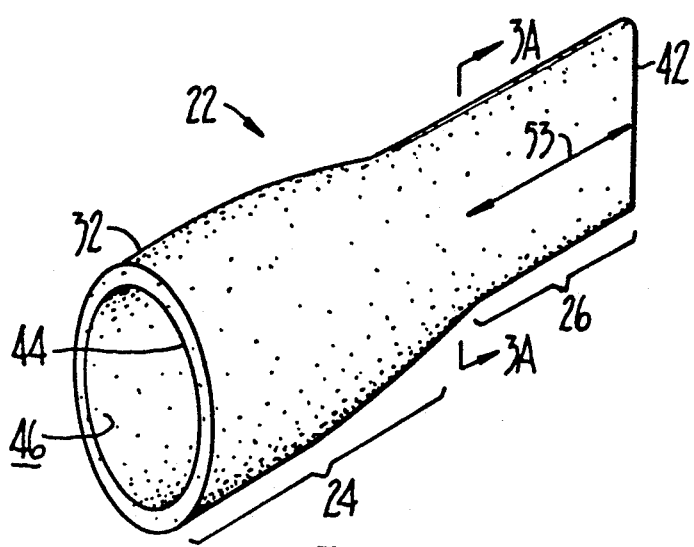
FIG. 3 is a perspective view of the simplified check valve of FIG. 1.

Referring now also to FIGS. 2 and 3, adapter 2 is shown to include a check valve 22 mounted within main bore 10. Check valve 22 is shown in a somewhat simplified form in FIGS. 1 through 3 to aid the discussion of its basic structure and function. Check valve 22 includes an entrance section 24 and a sealing section 26. Entrance section 24 seals main bore 10 along a first, diagonal position 28. This sealing can be achieved in many different ways. One way to do so is shown in FIG. 2 in which a rigid plastic sealing cap 30 is secured at second end 14 to capture the outer end 32 of check valve 22 between cap 30 and main bore 10. The inner end 34 of sealing cap 30 is oriented at an angle to main axis 36 of main bore 10; inner end 34 extends from a position 40 adjacent supplemental opening 20 to a position 41 diagonally opposite position 40 and axially forward, that is in the direction of arrow 38, of position 40. The outer end 43 of cap 30 has an inwardly tapering inner surface 45 which helps to guide catheter 6 into and through check valve 22.

The position and orientation of first, diagonal position 28, at which the sealing between check valve 22 and main bore 10 occurs, helps to eliminate dead space behind, that is in the reverse direction 42 of, supplemental opening 20. The elimination of dead space is also aided by the slight enlargement of bore 10 along first portion 28 (see FIG. 2) to help eliminate a small narrow pocket which might otherwise be created between check valve 22 and bore 10.

Entrance section 24 is shown to include an inwardly tapering interior 44 which helps guide therapeutic catheter 6 towards sealing section 26. The interior surface 46 of check valve 22 is preferably quite slippery so to provide very little hindrance to the insertion and removal of catheter 6 into and from adapter 2. This may be achieved by the selection of the material from which check valve 22 is made or by the coating of inner surface 46 with a material having good lubrication qualities. Also, a lubricant suitable for introduction into the patient's vascular system can be used within check valve 22.

Sealing section 26 includes, as illustrated in FIG. 3A, first and second sheets 48, 50 which abut along their inner surfaces. The thicknesses of sheets 48, 50 are exaggerated in FIG. 3A for sake of illustration. Sheets 48, 50 are flexible enough to conform to the shape of catheter 6 as shown in FIG. 3B, to seal at intersections 51. Sheets 48, 50 are preferably made from a relatively thin material having conforming, draping qualities similar to that exhibited by plastic wrap sold for home use.

The length 53 of sealing section 26 is preferably longer than two times the diameter 55 of catheter 6. The exact relative dimensions will depend upon various factors including the physical characteristics of sheets 48, 50 the strength of catheter 6, as well as the pressure and viscosity of the fluid occupying the space 57 between check valve 22 and main bore 10. In any event, length 53 is a substantial dimension, a substantial dimension being defined as at least twice the diameter of the smallest caliber therapeutic catheter to be used in conjunction with Y-adapter 2.

Figure 4A:
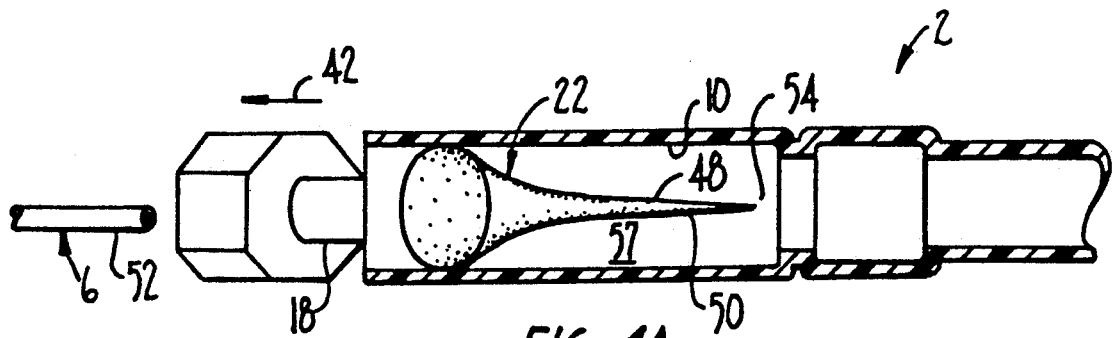
FIG. 4A is a simplified top view of the adapter of FIG. 1 showing the generalized configuration of the check valve before insertion of a therapeutic catheter.
Figure 4B:
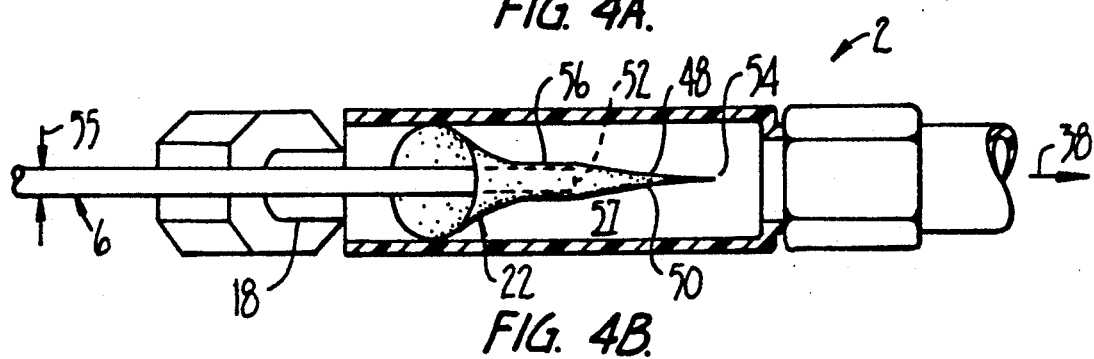
FIG. 4B illustrates the sealing effectiveness of the check valve with the tip of the therapeutic catheter partially inserted within the check valve.

Referring now to FIGS. 4A and 4B, simplified top views of Y-adapter 2 of FIG. 1 are shown before and during insertion of the end 52 of catheter 6 into check valve 22. The systemic blood pressure within space 57 in main bore 10 maintains sheets 48, 50 collapsed against one another in FIG. 4A so to prevent leakage of blood through check valve 22 in reverse direction 42. Partial insertion of end 52 of catheter 6 between sheets 48, 50, shown in FIG. 4B, creates a dual sealing action. The main seal against leakage of blood into check valve 22 is maintained at the valve exit 54 since the end 52 of catheter 6 has not yet caused sheets 48, 50 to separate at that point. However, in the region 56 of sealing section 26, sheets 48, 50 have already provided an effective seal against catheter 6 so that as catheter 6 continues to move in a forward direction 38 and finally opens valve exit 54, an effective seal against catheter 6 by sheets 48, 50 has already been produced to substantially eliminate leakage.

Figure 5:
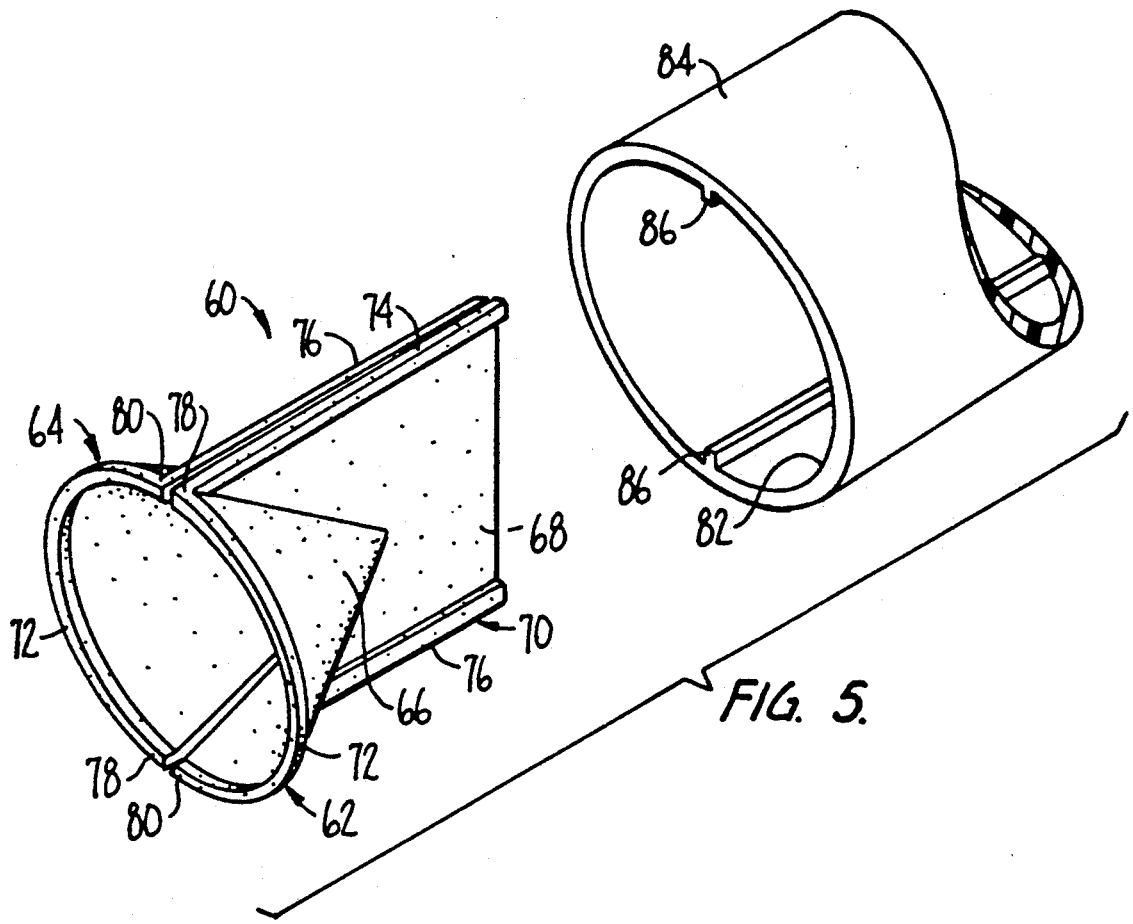
FIG. 5 is an enlarged view of an alternative embodiment of the simplified check valve of FIG. 3 illustrating a structural support for the check valve.

Referring now to FIG. 5, an alternative embodiment of check valve 22 of FIG. 1 is shown. Check valve 60 includes first and second elements 62, 64. Elements 62, 64 each include a tapered, semi-conical section 66 and a planar, sealing section 68. The shapes of sections 66, 68 for each element 62, 64 is maintained by a frame 70. Each frame 70 includes a semi-circular portion 72 and straight portions 74, 76 extending from the ends 78, 80 of semi-circular portion 72. With this embodiment, main bore 82 formed in body 84 includes a pair of longitudinally extending keys 86 formed opposite one another. Straight portions 74, 76 are positioned on either side of keys 86 and are fastened thereto, such as by ultrasonic welding or by using an adhesive.

Frames 70 help to keep sealing sections 68 in a desired at-rest configuration, typically generally flat, as illustrated in FIG. 5. To provide sufficient material to allow the desired conformance as shown in FIG. 3B, the desired at-rest configuration of sealing section 68 will likely be somewhat bowed or wavy, not taut. It may be desired to adjust the amount of material in each sealing section 68 according to a range of diameters of catheters 6 to be used with a particular adapter 2. Also, since the invention can be used with two or more therapeutic catheters 6, alone or in combination with devices such as guide wires, in a side-by-side relationship, this can also be accommodated through the amount of material in sealing section 68. Of course if the side edges of sealing section 68 were not radially restrained, such measures may not be necessary. Therefore, it may be desirable to limit the axial but not radial, movement of the sealing sections 26, 68.

At FIG. 6 an alternative embodiment of valve 60 is shown. Check valve 90 is similar to check valve 60 but uses 4 elements 88 instead of two as in check valve 60. This configuration would eliminate the above described conformance problems associated with check valve 60. Check valves with other numbers of valve elements could be used as well.

Referring also to FIG. 7, during angioplasty guiding catheter 4 is inserted into the vascular system of the patient, and connector 16 is used to connect Y-adapter 2 to the outer end 89 of the guiding catheter. A thin guide wire 90 is inserted through check valve 22 and through guiding catheter 4. A balloon catheter 92 is passed over guide wire 90, through check valve 22 and through sheath 4 until properly positioned. The dilation balloon 94 a the end of balloon catheter 92 is then inflated through an inflation device 96 coupled to balloon catheter 92 by another Y-adapter 98. Dilation balloon 94 is then deflated and guide wire 90 and balloon catheter are repositioned within the patient or are withdrawn through Y-adapter 2. Both adapter 2 and 98 may be similar in configuration.

Figure 8A:
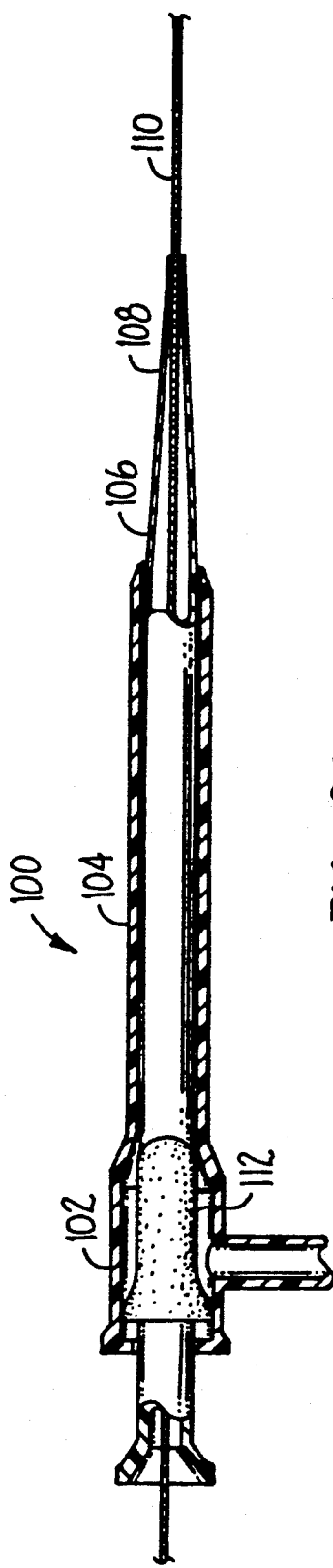
FIG. 8A illustrates another alternative embodiment of the invention with a guide wire and dilator sheath installed.
Figure 8B:
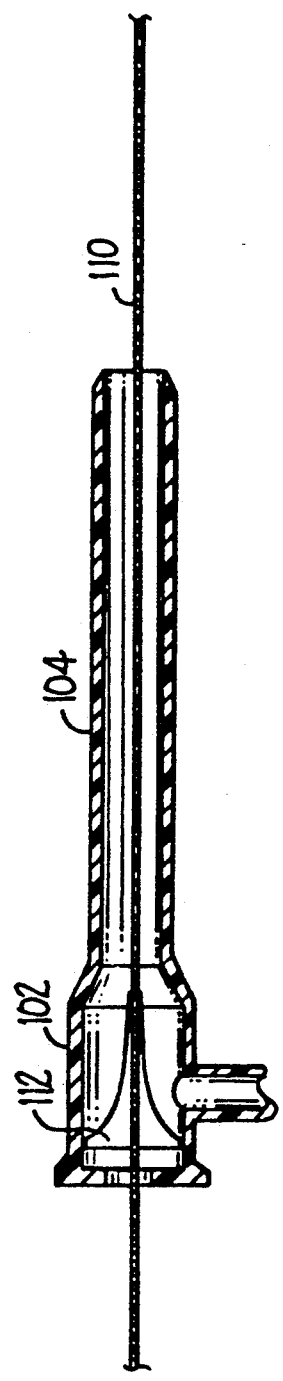
FIG. 8B illustrates the embodiment of FIG. 8A following removal of the dilator sheath.

Turning now to FIGS. 8A and 8B, the invention is shown used with an intravascular sheath assembly 100. Assembly 100 includes an adapter 102 having an integral guiding catheter 104. A dilation sheath 106, having a tapered inner end 108, passes through adapter 102 and guiding catheter 104 to aid insertion of guiding catheter 104 into an appropriate vascular structure. A guide wire 110 is shown passing through adapter 102, guiding catheter 104 and sheath 106. After guiding catheter 104 is introduced, sheath 106 is removed. See FIG. 8B. Assembly 100 includes a check valve 112 similar to check valve 22. Check valve 112 seals both the outer surface of sheath 106 as shown in FIG. 8A and then the outer surface of guide wire 110, as shown in FIG. 8B, in the same manner as check valve 22 seals therapeutic catheter 6.

Modification and variation can be made to the disclosed embodiments without departing from the subject of the invention as defined in the following claims. For example, check valves 22, 60, 80 have flexible entrance sections. If desired the entrance sections could be substantially rigid acting to guide therapeutic catheter, or other device, into the sealing section. Such entrance sections could be integral parts of body 8. However, by having the entrance section flexible, a variety of sizes and numbers of therapeutic catheters can be simply accommodated.

What is claimed is:

1. A therapeutic catheter apparatus, comprising:
   a therapeutic device having a first length;
   a guiding catheter having a hollow interior;
   an adapter adjacent said guiding catheter and contacting said therapeutic device having a main bore with first and second ends passing therethrough for introducing said therapeutic device into said guiding catheter; the adapter including a check valve positioned within the main bore for preventing fluid flow in a reverse direction from the first end to the second end, the check valve including an entrance section towards the second end of the main bore and a sealing section towards the first end of the main bore; and
   the sealing section including flexible, conformable sheets having abutting sealing surfaces between which the therapeutic device passes and external surfaces, the sealing surfaces having a second axial length, less than said first length, the sheets being adapted to conformingly engage the therapeutic device and form a seal therewith along the full extent of said second axial length said sealing surfaces formed of a comformable, low resilience material, having a resilience sufficiently low that when said external surfaces are subjected to a fluid pressure not exceeding human blood pressure, said seal is formed solely in response to said fluid pressure acting on the external surfaces of the sheets while exerting low frictional resistance to insertion and removal of the therapeutic device.

2. Apparatus for use in an intravascular procedure comprising:
   a therapeutic device having a first length,
   a guiding catheter having a hollow interior, an outer end and an inner end axially spaced from said outer end,
   an adaptor adjacent said guiding catheter and contacting said therapeutic device, for permitting the therapeutic device to be inserted into and removed from the guiding catheter, the adapter comprising:
   a body having a main bore passing therethrough, the main bore having a first end, with means for connection of the body to the outer end of the guiding catheter, and a second end, the body having at least a first wall portion;
   a check valve positioned within the main bore for preventing fluid in a reverse direction from the first end to the second end, the check valve including an entrance section towards the second end of the main bore and a sealing section towards the first end of the main bore; and
   the sealing section including flexible, conformable sheets having abutting sealing surfaces and external surfaces, the sealing surfaces having a second axial length, less than said first length,
   wherein at least a portion of said therapeutic device is positioned between said sheets and wherein said sheets conformingly engage the therapeutic device and form a seal therewith along the full extend of said second axial length, said sealing surfaces formed of a conformable, low-resilience material, having a resilience sufficiently low that when said external surfaces are subjected to a fluid pressure not exceeding human blood pressure, said seal is formed solely in response to said fluid pressure acting on the external surfaces of the sheets while exerting low frictional resistance to insertion and removal of the therapeutic device.

3. The apparatus of claim 2 wherein at least a part of the wall portion of the body defines a supplemental opening fluidly connected to the main bore.

4. The apparatus of claim 3 further comprising means for sealing the main bore adjacent the position of said supplemental opening to help eliminate dead space in the main bore between the position of said supplemental opening and the second end.

5. The apparatus of claim 4 wherein the sealing means engages the main bore along a line extending from a point adjacent the supplemental opening in a direction transversely away from the supplemental opening and axially towards the first end.

6. The apparatus of claim 5 further comprising a side conduit extending from the supplemental opening parallel to said direction.

7. The apparatus of claim 2 wherein the check valve includes means for maintaining the sheets in a desired at-rest configuration.

8. The apparatus of claim 7 wherein the sheets in the at-rest configuration includes generally flat regions.

9. The apparatus of claim 7 wherein the shape maintaining means include axially extending rigid supports.

10. The apparatus of claim 9 wherein the rigid supports connect the sheets to the main bore.

11. The apparatus of claim 2 wherein the check valve includes two of said sheets.

12. The apparatus of claim 2 wherein the entrance section is conical.

13. The apparatus of claim 2 wherein the entrance section is flexible.

14. The apparatus of claim 2 wherein said second axial length of the sealing section is at least two times the lateral dimension of the therapeutic device.

15. The apparatus of claim 2 wherein the body and check valve are sized to accept a removable dilation sheath therein, the dilation sheath aiding insertion of the guiding catheter into the patient's body.

16. Apparatus for use in an intravascular procedure comprising:
a therapeutic device having a first length, and a diametrical dimension,
a guiding catheter having a hollow interior, an outer end and an inner end axially spaced from said outer end,
an adapter adjacent said guiding catheter and contacting said therapeutic device, for permitting the therapeutic device to be inserted into the guiding catheter, the adapter comprising:
a body having a main bore passing therethrough, the main bore having a first end with means for connection of the boy to the outer end of the guiding catheter, and a second end, the body having at least a first wall portion;
a check valve positioned within the main bore for preventing fluid flow in a reverse direction from the first end to the second end, the check valve including an entrance section towards the second end of the main bore and a sealing section towards the first end of the main bore;
a supplemental opening defined by at least a part of the wall portion of the body, fluidly connected to the main bore to permit vascular pressure readings to be taken;
means for sealing the main bore adjacent to the position of said supplemental opening to help eliminate dead space in the main bore between the supplemental position and the second end;
the sealing means engaging the main bore along a line extending from a point adjacent the supplemental opening in a direction transversely away from the supplemental opening and axially towards the first end; and
the sealing section including flexible, conformable sheets having abutting sealing surfaces and external surfaces, the sealing surfaces having a second axial length of at least two times said diametrical dimension, the sheets being adapted to conformingly engage an inserted device and from a seal therewith along the full extent of said second axial length, said sealing surfaces formed of a comfortable, low-resilience material, having a resilience sufficiently low that when said external surfaces are subjected to a fluid pressure not exceeding human blood pressure, said seal is formed solely in response to said fluid pressure acting on the external surfaces of the sheets.

17. The apparatus of claim 16 wherein the check valve includes means for maintaining the sheets in a desired at-rest configuration.

* * * * *